US007205435B2

(12) United States Patent
Roques et al.

(10) Patent No.: US 7,205,435 B2
(45) Date of Patent: Apr. 17, 2007

(54) TYPE B BOTULISM TOXIN INHIBITORS

(75) Inventors: Bernard Roques, Paris (FR); Christine Anne, Chatenay Malabry (FR); Serge Turcaud, Sartrouville (FR); Marie-Claude Fournie-Zaluski, Paris (FR)

(73) Assignees: Institut National de la Sante et de la Recherche Medicale (INSERM), Paris (FR); Centre National de la Recherche Scientifique (C.N.R.C.), Paris (FR)

( * ) Notice: Subject to any disclaimer, the term of this patent is extended or adjusted under 35 U.S.C. 154(b) by 91 days.

(21) Appl. No.: 10/474,378

(22) PCT Filed: Apr. 10, 2002

(86) PCT No.: PCT/FR02/01258

§ 371 (c)(1), (2), (4) Date: Apr. 19, 2004

(87) PCT Pub. No.: WO02/083716

PCT Pub. Date: Oct. 24, 2002

(65) Prior Publication Data

US 2004/0176333 A1 Sep. 9, 2004

(30) Foreign Application Priority Data

Apr. 10, 2001 (FR) .................................. 01 04895

(51) Int. Cl.

| | |
|---|---|
| ***C07C 233/00*** | (2006.01) |
| ***C07C 235/00*** | (2006.01) |
| ***C07C 237/00*** | (2006.01) |
| ***C07C 231/00*** | (2006.01) |
| ***C07C 231/02*** | (2006.01) |
| ***C07C 231/08*** | (2006.01) |
| *C07K 5/06* | (2006.01) |
| *C07K 5/065* | (2006.01) |
| *C07K 5/068* | (2006.01) |
| *C07K 5/072* | (2006.01) |
| *A61K 31/195* | (2006.01) |
| *A61K 31/197* | (2006.01) |

(52) U.S. Cl. ...................... 564/123; 564/133; 530/300; 530/333; 514/2; 514/563

(58) Field of Classification Search ..................... None
See application file for complete search history.

(56) References Cited

U.S. PATENT DOCUMENTS

| | | | | |
|---|---|---|---|---|
| 4,407,794 | A * | 10/1983 | Roques et al. | 514/17 |
| 4,513,009 | A * | 4/1985 | Roques et al. | 514/513 |
| 4,618,708 | A * | 10/1986 | Roques et al. | 562/448 |
| 4,714,757 | A * | 12/1987 | Gordon et al. | 530/329 |
| 4,738,803 | A * | 4/1988 | Roques et al. | 562/623 |
| 4,985,406 | A * | 1/1991 | Charpentier et al. | 514/11 |
| 5,190,921 | A * | 3/1993 | Roques et al. | 514/17 |
| 5,466,672 | A * | 11/1995 | Kushnaryov et al. | 514/14 |
| 5,491,169 | A * | 2/1996 | Roques et al. | 514/529 |
| 5,591,891 | A * | 1/1997 | Fournie-Zaluski et al. | 562/426 |
| 5,741,781 | A * | 4/1998 | Roques et al. | 514/19 |
| 5,801,274 | A * | 9/1998 | Fournie-Zaluski et al. | 562/426 |
| 6,136,842 | A * | 10/2000 | Deprez et al. | 514/414 |
| 6,180,611 | B1 * | 1/2001 | Montana et al. | 514/19 |
| 6,340,708 | B1 * | 1/2002 | Llorens-Cortes et al. | 514/578 |
| 6,391,866 | B1 * | 5/2002 | Roques et al. | 514/119 |
| 6,518,260 | B1 * | 2/2003 | Fournie-Zaluski et al. | 514/141 |
| 6,716,852 | B2 * | 4/2004 | Roques et al. | 514/292 |

OTHER PUBLICATIONS

C. David-Basei, et al. J. Labelled Cpd. Radiopharm. (2001), 44, pp. 89-98.*
A.D. Baxter, et al. Bioorg. Med. Chem. Letters (1997) 7(21), pp. 2765-2770.*
E.J. Schantz and E.A. Johnson. Microbiol. Rev. (1992) 56(1), pp. 80-99.*
L.E. Davis. West. J. Med. (1993) 158, pp. 25-29.*
O. Resetto, et al. Toxicon (2001) 29, pp. 27-41.*
C.G. Knight, et al. FEBS Letters (1992) 296(3), pp. 2634-266.*
R.J. Bastin, et al. Org. Proc. Res. Develop. (2000) 4, pp. 427-435.*
L. Martin et al. J. Med. Chem. (1999) 42, pp. 515-525.*

* cited by examiner

*Primary Examiner*—Cecilia J. Tsang
*Assistant Examiner*—Andrew D. Kosar
(74) *Attorney, Agent, or Firm*—B. Aaron Schulman; Stites & Harbison PLLC

(57) ABSTRACT

Novel compounds of general formula (I), are provided with inhibitory properties for the type B botulism toxin activity, along with methods for preparation thereof and corresponding pharmaceutical compositions.

(I)

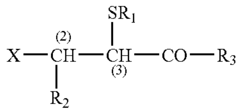

25 Claims, No Drawings

TYPE B BOTULISM TOXIN INHIBITORS

The present invention relates to novel compounds that have inhibitory properties on the activity of, type B botulinum toxin, to processes for preparing these compounds and to the corresponding pharmaceutical compositions.

The family of botulinum neurotoxins consists of seven proteins that are structurally similar but antigenically different (serotypes A to G) produced by different strains of anaerobic bacillus “Clostridium botulinum”. They are the most powerful toxins known, with lethal dose 50 values in mice of from 0.1 to 1 ng/kg. They act on the peripheral nervous system in man and various animal species by inducing “botulism”, which is characterized by a flaccid paralysis of the skeletal muscles, which may result in death. The two forms most frequently encountered are the botulinum toxins of types A and B. The major form of intoxication with the neurotoxins is caused by ingestion of contaminated food. However, these proteins, which are easy to produce, may also constitute a potential biological weapon. Finally, botulinum toxins A and B have been used in recent years for therapeutic applications in the context of dystonia, motor neuron hyperactivity, such as strabismus, blepharospasm, etc.

Botulinum neurotoxins consist of two subunits: a heavy chain (~100 kDa) associated with a light chain (~50 kDa) via a disulfide bridge. The heavy chain participates in the binding of the toxin to the nerve ending, in the internalization and then in the translocation of the light chain into the cytosol. The light chain is responsible for the toxicity of the protein via inhibition of the $Ca^{2+}$-dependent release of acetylcholine. The toxicity of the light chain is due to its peptidase activity. Specifically, botulinum toxins belong to the family of zinc metallopeptidases that contain the HExxH consensus sequence (Schiavo et al., 1992, *J. Biol. Chem.* 267(33), 23479–23483). They very specifically cleave the neuronal proteins involved in the exocytosis of neurotransmitters.

Type B botulinum toxin cleaves synaptobrevin (VAMP), a small protein of 116 amino acids that is embedded in the membrane of the small synaptic vesicles, at the Q76-F77 linkage.

The most effective approach for combating the harmful effects of BoNT/B toxin, either during a botulism outbreak or in the course of therapeutic contraindications, is the development of selective inhibitors with high affinity for the metallopeptidase activity of the toxin.

Some inhibitors of low efficacy have previously been described in the literature. Mention may be made of: i) buforine I and II (Garcia et al., 1999, *J. Applied Toxicology* 19 (Suppl 1) S19–S22) which inhibit BoNT/B with $IC_{50}$ values of $10^{-6}$ M and $2.5\times10^{-4}$ M, respectively; ii) ICD 1578 (7-N-phenylcarbamoylamino-4-chloro-3-propyloxycoumarin) $IC_{50}$=27 μM (Adler et al., 1998, *FEBS Lett.* 429, 234–238); iii) phosphoramidon, a neprylisin inhibitor, which tested in vivo on mouse phrenic nerve at an effective dose of 0.2 mM (Deshpaude et al., 1995, *Toxicon* 33, 551–557); iv) phosphonate analogs of phosphoramidon such as ICD 2821 (Adler et al., 1999, *J. Applied Toxicology* 16, S5–S11) which appear to be slightly more effective than phosphoramidon itself; v) finally, tetanus toxin inhibitors (Martin et al., 1999, *J. Med. Chem.* 42(3), 515–524) have shown micromolar activities on BoNT/B.

However, all these molecules are found to have little efficacy on BoNT/B toxin.

Thus, there is still a need for medicinal products for treating, in smaller doses, the diseases induced by botulinum toxin B.

The present invention aims, precisely, at proposing novel compounds capable of selectively inhibiting the enzymatic activity of botulinum toxin. These compounds are potential therapeutic agents against botulism.

More specifically, according to one of its aspects, the subject of the present invention is compounds having the following general formula (I), which are capable of selectively inhibiting botulinum toxin B with high affinity and selectivity for this toxin:

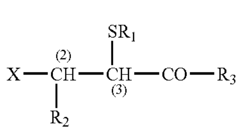

(I)

wherein:

(2) and (3) indicate two of the possible asymmetric centers in the molecule;

X represents a hydrogen atom, a primary amine $NH_2$ or secondary amine NHR with R representing an alkyl or arylalkyl group;

$R_1$ represents:

- a hydrogen atom,
- a group S—R' in which R' represents an alkyl, aryl, (aryl)alkyl, cycloalkyl or (cycloalkyl)alkyl group, optionally substituted with one or more halogen atoms, preferably fluorine, or a $CF_3$ group; or
- a group S—CH[CH($R_2$)X]—CO—$R_3$ with $R_2$, X and $R_3$ being as defined above or below;

$R_2$ represents an alkyl, alkenyl, alkynyl, cycloalkyl, (cycloalkyl)alkyl, aryl or (aryl)alkyl group, substituted with a COOH or COOR", $SO_3H$ or $SO_3R"$, $PO_3H_2$ or $PO_3R"_2$ group, with R" representing an alkyl, aryl, (aryl)alkyl, cycloalkyl or (cycloalkyl) alkyl group, optionally substituted with one or more halogen atoms, preferably fluorine, or a $CF_3$ group;

$R_3$ represents:

- a group $NHR_4$ in which $R_4$ represents an alkyl, cycloalkyl, (cycloalkyl)alkyl, aryl, (aryl)alkyl, heteroaryl or (heteroaryl)alkyl group; or
- a peptide chain $(AA)_nR_5$ in which:
  - n is equal to 1 or 2
  - $R_5$ is equal to OH, $NH_2$ or NHR'" with R'" representing an alkyl, cycloalkyl, (cycloalkyl)alkyl, aryl, (aryl)alkyl, heteroaryl or (heteroaryl)alkyl group,
  - AA represents an amino acid residue of formula (II)

$$N(R_6)—(CH_2)_m—CH(R_7)—(CH_2)_p—CO \quad (II)$$

- in which:
  - m=0 or 1, p=0 or 1,
  - $R_6$ represents a hydrogen atom or an alkyl group, preferably methyl, and
  - $R_7$ represents an alkyl, (aryl)alkyl or (heteroaryl) alkyl group, optionally substituted with one or more halogen atoms and/or one or more OH, alkoxy and preferably $OCH_3$, or $CF_3$ groups,
  - in which, when n is equal to 2, the two amino acid residues AA may be identical or different;

and the derivatives of these compounds of general formula (I).

The definitions of the various groups proposed in the general formulae (I) and (II) of the claimed compounds are specified in the list below. These definitions apply to the terms as they are used throughout this text (unless they are limited to specific examples) either individually or as forming part of a larger group.

Thus, in the scope of the invention, the following definitions apply:

alkyl: a linear or branched saturated aliphatic group containing from 1 to 6 carbon atoms;

cycloalkyl: a hydrocarbon-based ring containing 3, 4, 5 or 6 carbon atoms;

alkenyl: a linear or branched aliphatic chain of 2 to 6 carbon atoms containing at least one double bond;

alkynyl: an aliphatic chain of 2 to 6 carbon atoms containing at least one triple bond;

aryl: an aromatic ring containing 6 carbon atoms which are optionally fused and/or optionally substituted with one or two other aromatic rings containing 6 carbon atoms;

heteroaryl: an aromatic heterocycle with 5 or 6 atoms, containing one or two heteroatoms chosen from N, S and O, which is optionally fused to and/or optionally substituted with one or two aromatic rings containing 6 carbon atoms or heteroaromatic rings containing 5 or 6 atoms.

These groups may all be substituted with one or more halogen atom(s), hydroxyl group(s) or carboxylic or ester function(s).

According to the present invention, the term "derivatives" is intended especially to cover the addition salts of the compounds of general formula (I) obtained with acids, in particular pharmacologically acceptable organic or mineral acids. They may be, for example, salts such as the hydrochloride, hydrobromide, sulfate, nitrate, borate, phosphate, methanesulfonate, acetate, fumarate, succinate, ascorbate, oxalate, lactate, pyruvate, citrate, tartrate, maleate, malonate, benzoate, diaminobenzenesulfonate, chromoglycate, benzenesulfonate, cyclohexanesulfonate, toluenesulfonate, dipropylacetate, glucose-1-phosphate, palmoate and palmitate.

Among these derivatives, mention may also be made of the dimers of compounds of general formula (I), consisting of two molecules of compounds of general formula (I), which may be identical or different, coupled together via their respective sulfur atoms. In this particular case, $R_1$ is the group S—CH[CH($R_2$)X]—CO—$R_3$ identified above.

Similarly, the present invention extends to the various enantiomeric forms of the claimed compounds.

Specifically, the compounds of formula (I) may contain several asymmetric carbons, and thus exist in the form of racemic mixtures or diastereoisomeric mixtures, or alternatively in the form of pure stereoisomers.

At the very least, the compounds of general formula (I) contain the two asymmetric centers noted (2) and (3) on formula (I). The compounds may consequently exist in the form of four stereoisomers. These four stereoisomers form part of the invention.

The group $R_3$ may also contain one or more chiral centers. The (R) and (S) stereoisomers of each additional chiral center also form part of the invention.

The optically pure compounds may be isolated by enantioselective syntheses or resolutions with chiral amines. In the case of preparation processes leading to mixtures of stereoisomers, a separation by semipreparative HPLC on a column (Vydac $C_{18}$, 10×250 mm, $CH_3CN$—$H_2O$) is performed, allowing a separate biochemical and pharmacological study of each stereoisomer.

Among the stereoisomers that are preferred are those having an (S) absolute configuration on carbon (2) bearing the group $R_2$, and an (S) configuration on carbon (3) bearing the —SR function.

As preferred compounds according to the invention, mention may be made more particularly of the compounds of general formula (I) in which R represents either a hydrogen atom or a group S—CH[CH($R_2$)X]—CO—$R_3$ which may be identical to or different than the group featured by the general formula (I).

The compounds of general formula (I) with a significant hydrophobic nature have moreover been found to be most particularly advantageous for their inhibitory properties on botulinum toxin.

This hydrophobic nature is especially favorably induced by the presence of several alkyl groups and more preferably of groups of aryl and/or heteroaryl nature on the molecule of the compound of general formula (I).

In the present case, the compounds of general formula (I) in which the substituent $R_2$ features a group comprising at least one optionally fused aryl group are preferred according to the invention.

More preferably, $R_2$ represents an aryl or arylalkyl group substituted with at least one carboxylic function.

This hydrophobicity may moreover be reinforced by the presence of alkyl chain(s) and/or aryl and/or arylalkyl group(s) on the other substituents $R_1$ and $R_3$.

In the present case, according to one preferred embodiment of the invention, $R_1$ represents a group S—CH[CH($R_2$)X]—CO—$R_3$. The compound of general formula (I) then corresponds to the definition of a symmetrical disulfide.

As regards $R_3$, it preferably features a peptide chain $(AA)_nR_5$ with n preferably equal to 2, and more preferably m and p equal to zero.

According to one preferred variant, AA features a group of general formula (II) in which the two groups $R_7$, which are different than each other, represent an (aryl)alkyl or (heteroaryl)alkyl group.

Preferred compounds that may be mentioned more particularly are those having the general formula (Ia):

(Ia)

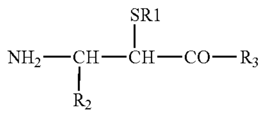

in which:

$R_1$ represents a hydrogen atom or, preferably, a group —S—CH[CH($R_2$)$NH_2$]$COR_3$ with $R_2$ and $R_3$ being as defined above or below;

$R_2$ represents a (cycloalkyl)alkyl, aryl or (aryl)alkyl group, substituted with at least one COOH function;

$R_3$ represents either a group $NHR_4$ with $R_4$ representing an alkyl, cycloalkyl, (cycloalkyl)alkyl, aryl, (aryl)alkyl, heteroaryl or (heteroaryl)alkyl group or a group of formula (IIa):

$$[NH(CH_2)_m—CHR_7—(CH_2)_p]_nCOR_5 \quad \text{(IIa)}$$

in which:

- n is equal to 1 and preferably 2, in which, when n is equal to 2, the two groups given within the square brackets may be identical or different;
- $R_7$ represents an (aryl)alkyl or (heteroaryl)alkyl group, optionally substituted with one or more halogen atoms and/or OH, $OCH_3$ or $CF_3$ group(s),
- $R_5$ represents an $NH_2$ or NHR''' group in which R''' represents an alkyl, aryl, (aryl)alkyl, cycloalkyl or (cycloalkyl)alkyl group, optionally substituted with one or more halogen atoms, preferably fluorine, or a $CF_3$ group, and
- m or p, which may be identical or different, represents 0 or 1.

According to one preferred embodiment of the invention, m and p are equal to zero and more preferably n is equal to 2.

As regards the group featured by $R_7$ in the general formula (II) or (IIa), it is preferably chosen from benzylnaphthylmethyl, benzothienylmethyl, indolylmethyl and biphenylmethyl.

When n is equal to 2, the two groups $R_7$ are preferably different.

As an illustration of the claimed compounds according to the invention, mention may be made more particularly of the following derivatives:

- (2S,3S)-2-(p-methoxybenzyl)sulfenyl-3-N-Boc-amino-4-(4-t-butyloxycarbonyl)phenylbutanoic acid;
- N-[(2S,3S)-2-sulfanyl-3-amino-4-(4-carboxy)phenylbutanoyl] Trp-Phe;
- N-[(2S,3S)-2-sulfanyl-3-amino-4-(4-carboxy)phenylbutanoyl] Trp-Phe benzamide;
- N-[(2S,3S)-2-sulfanyl-3-amino-4-(4-carboxy)phenylbutanoyl] (N-Me)Trp-Phe benzamide;
- N-[(2S,3S)-2-sulfanyl-3-amino-4-(4-carboxy)phenylbutanoyl] Bip-Tyr benzamide;
- N-[(2S,3S)-2-sulfanyl-3-amino-4-(4-carboxy)phenylbutanoyl] Bip-His benzamide;
- N-[(2S,3S)-2-sulfanyl-3-amino-4-(4-carboxyl)phenylbutanoyl] Bip-Phe-benzamide;
- N-[(2S,3S)-2-sulfanyl-3-amino-4-(4-carboxy)phenylbutanoyl] Bip-D-Phe benzamide;
- N-[(2S,3S)-2-sulfanyl-3-amino-4-(4-carboxy)phenylbutanoyl]-D-Bip-Phe benzamide;
- N-[(2S,3S)-2-sulfanyl-3-amino-4-(4-carboxy)phenylbutanoyl] Bip-Ile benzamide;
- N-[(2S,3S)-2-sulfanyl-3-amino-4-(4-carboxy)phenylbutanoyl] 1-Nap-Phe benzamide;
- N-[(2S,3S)-2-sulfanyl-3-amino-4-(4-carboxy)phenylbutanoyl] Bip-Bta benzamide;
- N-[(2S,3S)-2 benzyldisulfanediyl-3-amino-4-(4-carboxy)phenylbutanoyl] Bip-Bta benzamide;
- (2S)-2,2'-disulfanediyl bis[(3S)-3-amino-4-(4-carboxy)phenylbutanoyl]bis(Bip-Tyr benzamide);
- (2S)-2-2'-disulfanediylbis[(3S)-3-amino-4-(4-carboxy)phenylbutanoyl]bis(Bip-Ile benzamide);
- (2S)-2-2'-disulfanediylbis[(3S)-3-amino-4-(4-carboxy)phenylbutanoyl]bis(Bip-Phe benzamide);
- (2S)-2-2'-disulfanediylbis[(3S)-3-amino-4-(4-carboxy)phenylbutanoyl]bis(Bip-Bta benzamide);
- (2S)-2,2'-dilsulfanediylbis[(3S)-3-amino-4-(4-carboxy)phenylbutanoyl]bis(benzamide);
- (2S)-2,2'-disulfanediylbis[4-(4-carboxy)phenylpropanoyl]bis(benzamide);
- (2S)-2,2'-disulfanediylbis[4-(4-carboxy)phenylpropanoyl]bis(Bip benzamide);
- (2S)-2,2'-disulfanediylbis[(3S)-3-amino-4-(4-carboxy)phenylbutanoyl)bis(1-naphthylmethyl amide);

and preferably

- (2S)-2-2'-disulfanediylbis((3S)-3-amino-4-(4-carboxy)phenylbutanoyl]bis(Bip benzamide); or
- (2S)-2,2'-disulfanediylbis[4-(4-carboxy)phenylpropanoyl]bis(Bip Bta benzamide).

A subject of the present invention is also the preparation of the claimed compounds.

The compounds of general formula (I) for which $X=NH_2$ are obtained from the intermediate of formula (III)

(III)

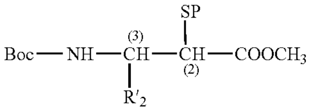

in which:

P is a thiol-protecting group, preferably para-methoxybenzyl

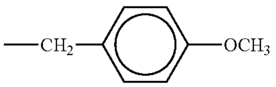

and

- $R'_2$ represents the protected form of $R_2$ on its functional group, it being understood that if $R_2$ contains a COOH group, $R'_2$ contains a COOtBu group;
- if $R_2$ contains an $SO_3H$ group, $R'_2$ contains an $SO_3CH_2tBu$ group;
- if $R_2$ contains a $PO_3H_2$ group, $R'_2$ contains a $PO_3(CH_2\phi)_2$ group;
- said compound being obtained by sulfenylation of the β-amino ester of formula (IV):

(IV)

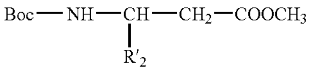

This sulfenylation reaction is performed by the action of 2,4-dinitrophenyl p-methoxybenzyl disulfide according to the process described by Bischoff et al. (1997, *J. Org. Chem.* 62, 4848–4850).

The α-amino ester of formula (IV) is obtained via a homologation reaction according to Arndt-Eisert (Meier et al., 1975, *Angew. Chem. Int. Ed. Engl.* 14, 32–43) of the N-protected α-amino acid of formula (V).

(V)

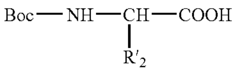

These N-protected α-amino acids are generally not commercially available, and are synthesized enantioselectively via the standard Oppolzer method (1957, *Tetrahedron* 43(9), 1969–2004), which involves the camphorsultam chiral synthon of formula (VI) and a halo, preferably bromo, derivative of formula (VII):

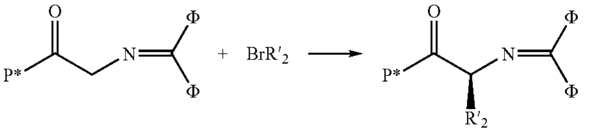

(VI) (VII) (VIII)

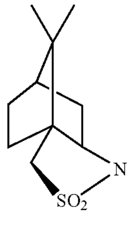

with P* being

By using the standard methods for deprotecting the camphorsultam intermediate of formula (VIII) and the standard reprotection of the free amine function in the form of a Boc group via the action of $(Boc)_2O$ (1993, *Synth. Commun.* 23, 1443), the compound of formula (V) is isolated in enantiomerically pure form.

If the amino acid of formula (V) is of S configuration, the homologation of formula (V) to formula (IV) taking place with retention of configuration, formula (IV) preferentially has the S configuration. The sulfenylation reaction of formula (IV) to give formula (III) is essentially a trans-addition. The compound of formula (III) then preferentially has the 2S, 3S configuration.

The deprotection of the methyl ester function of formula (III) to give formula (IX) is performed either via the action of aqueous sodium hydroxide in the presence of methanol, and in this case racemization of the chiral carbon in position 2 is observed, or via the action of BBTO (bis(tributyltin) oxide or tributyltin oxide (Salomon et al., 1994, *J. Org. Chem.* 59, 7259–7266), which allows the initial 2S, 3S configuration to be conserved.

(IX)

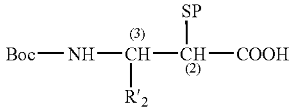

The couplings of the synthon of formula (IX) with the various groups $R_3$ containing an amide function are performed according to the standard methods of peptide synthesis.

Typically, this reaction is performed in dichloromethane or dimethylformamide, by the action of EDCI (1-(3-dimethylaminopropyl)-3-ethylcarbodiimide methiodide) in the presence of HOBt (1-hydroxybenzotriazole) or BOP (benzotriazol-1-yloxytris(dimethylamino)phosphonium hexafluorophosphate) at room temperature in the presence of a tertiary amine such as diisopropylethylamine.

When $R_3$ represents an amino acid or a peptide, the C-terminal carboxylate is protected in the form of a t-butyl ester.

The final deprotection of all the protecting groups is conventionally obtained in a single step by the action of HF at 0° C. in the presence of dimethyl sulfide, anisole and para-thiocresol.

The symmetrical disulfide corresponding to the general formula (I) for which $R_1$ is S—CH(CH($R_2$)X)—CO—$R_3$ is obtained by the action of an ethanolic solution of iodine on the compound of general formula (I) in which $R_1$ represents a hydrogen atom.

The dissymmetric disulfide corresponding to the general formula (I) in which $R_1$ features a group SR' is obtained by the action on the compound of general formula (I), in which $R_1$=H, of an activated disulfide of formula (X):

$R'—S—S—COOCH_3$ (X)

in which R' is as defined in the general formula (I).

The compound of formula (X) is conventionally formed by the action of a mercaptan of formula R'SH on methoxycarbonylsulfenyl chloride ($CH_3O_2CSCl$; Aldrich) in the presence of a tertiary amine such as trimethylamine in solution in a chloroform/methanol mixture.

The compounds of general formula (I) for which X=H are obtained from the synthon of formula (XI) in which $R'_2$ represents a protected form of $R_2$ as defined above.

(XI)

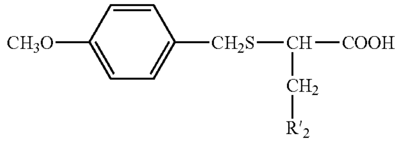

The compound of formula (XI) is typically prepared in two steps from an α-amino acid of formula (XII) according to the following reaction scheme

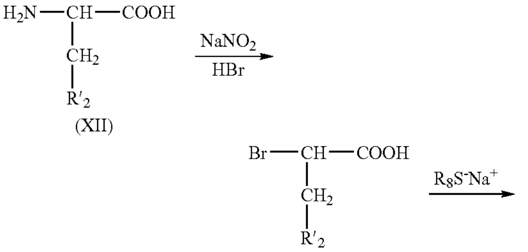

(XII) (XIII) (XI)

in which $R_8$=$CH_3CO$ or

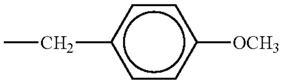

The α-amino acid of formula (XII) undergoes the standard halogenating deamination via the action of sodium nitrite in the presence of hydrobromic acid. This reaction generally takes place with retention of configuration.

The compound of formula (XIII) then undergoes a nucleophilic substitution of $SN_2$ type via the action of the sodium salt of para-methoxy-α-toluenethiol ($CH_3O$-φ-$CH_2SH$; Aldrich).

The synthon of formula (XI) is then coupled with various compounds corresponding to the general formula for $R_3$ via the protocol described above, to give the various compounds of general formula (I) in which X=H.

The claimed compounds are found to be capable of significantly inhibiting the enzymatic activity of type B botulinum toxin. In this respect, the claimed compounds may be used therapeutically in any pathological process induced via this toxin.

More specifically, the clinical applications for which the use of these compounds may be envisioned include diseases initiated by botulinum toxin BoNT/B.

To this end, the claimed compounds and the derivatives thereof may be used for the preparation of corresponding pharmaceutical compositions.

More particularly, according to another of its aspects, the present invention relates to a pharmaceutical composition comprising as active principle at least one compound of general formula (I) or a derivative thereof.

Needless to say, this compound may be combined therein with at least one pharmaceutically acceptable vehicle.

It may also be envisioned to covalently bond the compound of general formula (I) to a peptide (Tat sequence, penetratin sequence, etc.) in order especially to vectorize it into the cell.

Similarly, it is possible to combine two or more compounds of general formula (I) in the same pharmaceutical composition.

These pharmaceutical compositions may be administered orally, parenterally, sublingually, transdermally or topically.

As regards oral or sublingual administration, plain or sugar-coated tablets, gel capsules, granules possibly with delayed release, drops or liposomes are used in particular. As regards intravenous, subcutaneous or intramuscular administration, use is made of sterile or sterilizable solutions in particular for venous perfusion, while conventional patches may be produced for transdermal administration. Creams or lotions to be spread on the skin may be used for topical use.

The pharmaceutical compositions according to the present invention may be prepared according to usual methods that are well known in pharmaceutical technology.

The active principle may be incorporated into the excipients usually used in these pharmaceutical compositions, such as talc, gum arabic, lactose, starch, magnesium stearate, aqueous or nonaqueous vehicles, fatty substances of animal or plant origin, paraffin derivatives, glycols, and various wetting agents, dispersants, emulsifiers, preserving agents, etc.

The amount of active principle to be administered per day obviously depends on the particular nature of the therapeutic indication, the severity of the complaints to be treated, and also the patient's weight and the route of administration.

For systemic administration, the overall dose in man generally ranges between 1 and 100 mg per day, for example from 2 to 50 mg and more suitably from 3 to 40 mg per day.

Unit dosage forms for systemic administration will generally comprise from 3 to 50 mg (i.e. 3, 5, 10, 20, 30, 40 and 50 mg of product). These unit doses will be administered especially one or more times a day, preferably one to three times a day.

For topical administration, the pharmaceutical compositions generally contain from 0.0001% to 10% and preferably from 0.01% to 5% of active principle.

Besides this use of the compounds of general formula (I) as potential therapeutic agents for diseases induced by the toxin BoNT/B, their combined use with the toxin may also be envisioned, for example, for therapeutic purposes.

Specifically, methods for the symptomatic therapeutic treatment of dystonia by motor neuron hyperactivity have been developed in human clinical medicine. This type of prophylaxis is in particular proposed for treating disorders such as strabismus, blepharospasm, writer's cramp and hemifacial spasm. The therapy consists in injecting doses of clostridial toxins into the treated body. It is clear that, given the toxic nature of these toxins, the doses used must be minimized in order to prevent any harmful side effect. The coadministration of a compound according to the invention with a toxin thus offers the possibility of employing larger and thus more effective doses of these toxins.

Consequently, the compounds according to the invention advantageously provide an antidote to any undesired activity of the toxin BoNT/B, administered in human clinical medicine.

The development of a coadministration protocol for detecting and/or assaying the activity of these toxins in defined target muscles to achieve the desired clinical result may also be envisioned.

Consequently, a subject of the present invention is also the combined use of at least one compound of general formula (I) with at least one clostridial toxin such as botulinum neurotoxin, and the invention proposes a pharmaceutical composition comprising at least one compound of general formula (I) as a mixture with at least one clostridial toxin.

The compounds described according to the invention may also be used in the context of nontherapeutic applications, in particular in systems for diagnosing and detecting botulinum neurotoxin.

The examples given below in a nonlimiting manner will demonstrate other advantages of the present invention.

PREPARATION PROCESSES

The HPLC analyses of the finished products are performed on a Shimatzu® machine with a 5 μm, 100 Å Kromasil® ($C_8$ or $C_{18}$) column (flow rate 1 ml/minute, λ 210 nm) (250×4.6 mm or 150×4.6 mm).

The eluent consists of a mixture in variable proportions of solutions A and B. A (0.05% TFA in $H_2O$); B ($CH_3CN/H_2O$ (0.038% TFA)=9/1).

The Following Abbreviations Have Been Used

Bip: (L)Biphenylalanine
1Nap: (L)1-naphthylalanine
Bta: (L)Benzothienylalanine

EXAMPLE 1

Synthesis of (2S,3S)-2-(p-methoxybenzyl)sulfenyl-3-N-Boc-amino-4-(4-t-butyloxycarbonyl)phenylbutanoic acid Step 1. Synthesis of (2S)-2-(N-Boc)amino-3-[4-t-butyloxycarbonyl]phenylpropanoic acid A solution in THF of 33.5 g (78.6 mM) of the Oppolzer chiral couple is cooled to −78° C. under argon. 33 ml (1.05 eq) of nBuLi (2.5 M in hexane) are successively added, followed by addition, 15 minutes later, of a solution of 25 g (1.2 eq) of t-butyl 4-bromomethylbenzoate [obtained by the action of N-bromosuccinimide on para-toluic acid t-butyrate (Wohl-Zieyler & S. Pizey reaction. *Synthesis reagents*, Vol. 2, New York, 1974, pp. 1–63)] in 250 ml of a THF/HMPA mixture. The mixture is stirred at room temperature for 3 hours. The reaction is stopped by addition at 0° C. of 30 ml of a 4/1 THF/AcOH mixture. The mixture is concentrated under vacuum, taken up in 600 ml of ether and washed with 10% $NH_4Cl$ solution, with water and then with saturated NaCl solution. After drying over $Na_2SO_4$, the solution is evaporated to dryness. A yellow oil is obtained, which is purified by chromatography. White solid, 34.1 g (71%). m.p. 174° C.; $R_f$ (c.hex./EtOAc=7/3) 0.51.

The amine function of the above compound (32 g) is then deprotected in THF solution via the action of 540 ml of 10% citric acid. After 2 hours at room temperature, the THF is evaporated off under vacuum and the aqueous phase is washed three times with ether. The aqueous phase is then brought to pH 8 by adding 10% $NaHCO_3$ and the expected product is extracted with $CH_2Cl_2$. After drying and evaporation to dryness, 20.7 g (88%) of a colorless oil that crystallizes slowly are obtained.

20.7 g of the above compound are then dissolved in 200 ml of DMF. 11.65 ml of triethylamine and 9.94 g of $(Boc)_2O$ are then added at 0° C. After leaving overnight at room temperature, the solution is evaporated to dryness, taken up in ethyl acetate, washed with 10% $KHSO_4$, $H_2O$ and saturated NaCl, and dried over $Na_2SO_4$. After evaporation to dryness and chromatography on silica gel, 16.3 g (70%) of a white foam are obtained $R_f$ (c.hex./EtOAc/$CH_2Cl_2$=7/1.5/1.5) 0.21. The chiral auxiliary is cleaved from the above product (16.3 g) via the action of a solution of 2.78 g of LiOH, 12.57 g of LiBr and 3.73 g of $(nBu)_4NBr$ in 300 ml of acetonitrile. After stirring for 18 hours at room temperature, the mixture is evaporated to dryness, taken up in water and washed with ether. The aqueous phase is then acidified with 10% $KHSO_4$ and extracted with $CH_2Cl_2$. After chromatography on silica gel, a white foam is obtained (7.5 g, 71%). $R_f$ (c.hex./EtOAc/AcOH=5/5/0.5) 0.75.

Step 2. Synthesis of methyl (3S)-3-(N-Boc)amino-4-[4-t-butyloxycarbonyl]phenylbutanoate A solution in 60 ml of THF of 7.2 g of the above N-Boc α-amino acid is stirred at −20° C. under argon for 15 minutes with 2.6 ml of isobutyl chloroformate. The precipitate is removed rapidly and 110 ml of diazomethane are added to the solution. After 2 hours at room temperature, the mixture is evaporated to dryness. The residue is taken up in 180 ml of methanol, 0.32 g of PhCOOAg and 8.5 ml of triethylamine are added, and the mixture is stirred at 0° C. for 15 minutes and at room temperature for 30 minutes. The resulting mixture is filtered and evaporated to dryness, and the residue is taken up in ether. The ether solution is washed with saturated NaCl, dried over $Na_2SO_4$ and evaporated to dryness. Yellow solid, 5.7 g (73%). m.p.=71° C.

Step 3. Methyl (2S,3S)-2-(p-methoxybenzyl)sulfenyl-3-N-Boc-amino-4-(4-t-butyloxycarbonyl)phenyl butanoate At 0° C. under argon, 15.25 ml of BuLi (2.5 M in hexane) are added to a mixture of 7.5 ml of freshly distilled HMDS and 90 ml of anhydrous THF. After 15 minutes at 0° C., the solution is cooled to −70° C. and a solution of 5 g of the above N-Boc β-amino ester in 50 ml of anhydrous THF is added. After 2 hours at −70° C., 4.4 ml of HMDA and 6.3 g of (p-methoxybenzyl-2,4-dinitrophenyl)disulfide are added and the mixture is stirred for 1 hr 30 minutes at the same temperature. The reaction mixture is then poured onto a 50/50 1N HCl/$Et_2O$ mixture. The precipitate is removed. The organic phase is washed with water and with saturated NaCl. It is dried over $Na_2SO_4$ and evaporated to dryness. The red oil is purified by chromatography on silica (c.hex/$CH_2Cl_2$/EtOAc=8/1/1). A yellow oil that crystallizes is obtained, 3.84 g (54%). m.p.=79° C.

Step 4. (2S,3S)-2-p-methoxybenzylsulfenyl-3-N-Boc-amino-4-(4-t-butyloxycarbonyl)phenylbutanoic acid A solution of 3.7 g of the above ester dissolved in 13.5 ml of acetonitrile is added to a solution of 20.3 ml of tributyltin oxide (TBTO) in 80 ml of acetonitrile. The mixture is refluxed for 5 hours. The resulting mixture is cooled to 0° C. and 50 ml of HCl are added over 2 hours. After 3 hours at room temperature, the mixture is extracted with 25 ml of EtOAc. The organic extracts are washed with $H_2O$ and with saturated NaCl, dried over $Na_2SO_4$ and evaporated to dryness. The product is purified by chromatography on silica gel (c.hex./EtOAc/AcOH=8/2/0.5). Yellow solid, 2.85 g (79%). $T_r$=[$C_{18}$ Kromasil 5 μM/100 Å, 250×4.6 mm, 80% $CH_3CN$/20% $H_2O$ (0.05% TFA), 1 ml/min]=6.1 min.

EXAMPLE 2

N-[(2S,3S)-2-sulfanyl-3-amino-4-(4-carboxy)phenylbutanoyl] Trp-Phe

Step 1. A solution of the synthon described in example 1 (1 eq), of the dipeptide Trp-PheOtBu (1 eq), of HOBT (1-hydroxybenzotriazole, 1 eq), of diisopropylethylamine (1.2 eq) and of (1-(3-dimethylaminopropyl)-3-ethylcarbodiimide methiodide (EDCI, 4 eq) is prepared in the minimum amount of DMF and is stirred for 2 days at room temperature. The solvent is evaporated off and the residue is taken up in ethyl acetate, washed under the standard conditions for peptide coupling, dried and evaporated to dryness.

Step 2. The fully protected pseudopeptide is placed in contact with 5 μl/mg of dimethyl sulfide, 5 μl/mg of anisole and 1 μl/mg of p-thiocresol, and is placed in the reactor, into which HF is distilled at 0° C. After reaction for 1 hour at 0° C., the HF is evaporated off and the residue is precipitated in an ether/hexane mixture at −20° C. The solid is then dissolved in water and freeze-dried. The residue is purified by HPLC on a $C_8$ Kromasil 5 μM, 100 Å, 250×4.6 mm column, with a gradient of 30 minutes from 30 to 90% of B, 1 ml/minute, $T_r$=13.5 minutes. Mass=$MH^+$ 589.3.

EXAMPLE 3

N-[(2S,3S)-2-sulfanyl-3-amino-4-(4-carboxy)phenylbutanoyl] Trp-Phe benzamide This compound is prepared according to the protocol described in example 2, using in the first step the dipeptide amide Trp-Phe-NHBzl instead of the dipeptide ester Trp-PheOtBu. HPLC on $C_8$ Kromasil 5 μM, 100 Å, 250×4.6 mm column, 1 ml/minute, $T_r$ (55% of B)=5.2 minutes. Mass $MH^+$=678.4.

EXAMPLE 4

N-[(2S,3S)-2-sulfanyl-3-amino-4-(4-carboxy)phenylbutanoyl] (N-Me)Trp-Phe benzamide This compound is prepared according to the protocol described in example 2, using in the first step the dipeptide amide (N-Me) Trp-PheNHBzl instead of the dipeptide ester Trp-PheOtBu. HPLC on a $C_8$ Kromasil 5 μM, 100 Å, 250×4.6 mm column, 1 ml/minute, $T_r$ (50% of B)=7.4 minutes. Mass $MH^+$=692.6.

EXAMPLE 5

N-[(2S,3S)-2-sulfanyl-3-amino-4-(4-carboxy)phenylbutanoyl] Bip-Tyr benzamide This compound is prepared according to the protocol described in example 2, using in the first step the dipeptide amide Bip-Tyr-NHBzl instead of the dipeptide ester Trp-PheOtBu. HPLC on $C_8$ Kromasil 5 μM, 100 Å, 250×4.6 mm column, 1 ml/minute, $T_r$ (gradient from 40 to 100% of B over 20 minutes)=11.1 minutes. Mass $MH^+$=731.

EXAMPLE 6

N-[(2S,3S)-2-sulfanyl-3-amino-4-(4-carboxy)phenylbutanoyl] Bip-His benzamide

This compound is prepared according to the protocol described in example 2, using in the first step the dipeptide amide Bip-His-NHBzl instead of the dipeptide ester Trp-PheOtBu. HPLC on $C_8$ Kromasil 5 μM, 100 Å, 250×4.6 mm column, 1 ml/minute, $T_r$ (35% of B)=6.2 minutes. Mass $MH^+$=705.3.

EXAMPLE 7

N-[(2S,3S)-2-sulfanyl-3-amino-4-(4-carboxy)phenylbutanoyl] Bip-Phe benzamide

This compound is prepared according to the protocol described in example 2, using in the first step the dipeptide amide Bip-Phe-NHBzl instead of the dipeptide ester Trp-PheOtBu. HPLC on $C_8$ Kromasil 5 μM, 100 Å, 250×4.6 mm column, 1 ml/minute, $T_r$ (60% of B)=13.2 minutes. Mass $MH^+$=715.5.

EXAMPLE 8

N-[(2S,3S)-2-sulfanyl-3-amino-4-(4-carboxy)phenylbutanoyl] Bip-D-Phe benzamide

This compound is prepared according to the protocol described in example 2, using in the first step the dipeptide amide Bip-D-Phe-NHBzl instead of the dipeptide ester Trp-PheOtBu. HPLC on $C_8$ Kromasil 5 μM, 100 Å, 250×4.6 mm column, 1 ml/minute, $T_r$ (gradient from 40 to 100% of B over 20 minutes)=13.2 minutes. Mass $MH^+$=715.5.

EXAMPLE 9

N-[(2S,3S)-2-sulfanyl-3-amino-4-(4-carboxy)phenylbutanoyl]-D-Bip-Phe benzamide

This compound is prepared according to the protocol described in example 2, using in the first step the dipeptide amide D-Bip-Phe-NHBzl instead of the dipeptide ester Trp-PheOtBu. HPLC on $C_8$ Kromasil 5 μM, 100 Å, 250×4.6 mm column, 1 ml/minute, $T_r$ (gradient from 40 to 100% of B over 20 minutes)=12.6 minutes. Mass $MH^+$=715.6.

EXAMPLE 10

N-[(2S,3S)-2-sulfanyl-3-amino-4-(4-carboxy)phenylbutanoyl] Bip-Ile benzamide

This compound is prepared according to the protocol described in example 2, using in the first step the dipeptide amide Bip-Ile-NHBzl instead of the dipeptide ester Trp-PheOtBu. HPLC on $C_8$ Kromasil 5 μM, 100 Å, 250×4.6 mm column, 1 ml/minute, $T_r$ (gradient from 40 to 100% of B over 20 minutes)=11 minutes. Mass $MH^+$=680.

EXAMPLE 11

N-[(2S,3S)-2-sulfanyl-3-amino-4-(4-carboxy)phenylbutanoyl] 1-Nap-Phe benzamide

This compound is prepared according to the protocol described in example 2, using in the first step the dipeptide amide 1-Nap-Phe-NHBzl instead of the dipeptide ester Trp-PheOtBu. HPLC on $C_8$ Kromasil 5 μM, 100 Å, 250×4.6 mm column, 1 ml/minute, $T_r$ (50% of B)=7.4 minutes. Mass $MH^+$=689.5.

EXAMPLE 12

N-[(2S,3S)-2-sulfanyl-3-amino-4-(4-carboxy)phenylbutanoyl] Bip-Bta benzamide

This compound is prepared according to the protocol described in example 2, using in the first step the dipeptide amide Bip-Bta-NHBzl instead of the dipeptide ester Trp-PheOtBu. HPLC on $C_8$ Kromasil 5 μM, 100 Å, 250×4.6 mm column, 1 ml/minute, $T_r$ (gradient from 55 to 100% of B over 15 minutes)=8.9 minutes. Mass $MH^+$=771.7.

EXAMPLE 13

N-[(2S,3S)-2-benzyldisulfanediyl-3-amino-4-(4-carboxy)phenylbutanoyl] Bip-Bta benzamide This compound is prepared via the action of the active disulfide $BzCH_2S$—$SCOOCH_3$ (obtained via the action of methoxycarbonylsulfenyl chloride on benzyl mercaptan) on compound 12 in the presence of triethylamine dissolved in $CCl_4$. The product is purified by HPLC on a $C_8$ Kromasil 5 μM, 100 Å, 250×4.6 mm column, 1 ml/minute, $T_r$ (gradient from 40 to 100% of B over 20 minutes)=16.1 minutes. Mass $MH^+$=893.2.

EXAMPLE 14

(2S)-2-2'-disulfanediylbis[(3S)-3-amino-4-(4-carboxy)phenylbutanoyl]bis(Bip-Tyr benzamide)

This compound is obtained by treating the compound of example 6 with a $10^{-2}$ M solution of iodine in ethanol, dissolved in an acetonitrile/water mixture until a yellow coloration persists. The mixture is evaporated to dryness; the product is freeze-dried. HPLC on a $C_8$ Kromasil 5 μM, 100 Å, 250×4.6 mm column, 1 ml/minute, $T_r$ (gradient from 40 to 100% of B over 20 minutes)=19 minutes. Mass $MH^+$=1461.1.

EXAMPLE 15

(2S)-2-2'-disulfanediylbis[(3S)-3-amino-4-(4-carboxy)phenylbutanoyl]bis(Bip-Ile benzamide)

This compound is obtained from compound 11 according to the protocol described in example 14. HPLC on a $C_8$ Kromasil 5 μM, 100 Å, 250×4.6 mm column, 1 ml/minute, $T_r$ (gradient from 40 to 100% of B over 20 minutes)=13.6 minutes. Mass $MH^+$=1360.2.

EXAMPLE 16

(2S)-2-2'-disulfanediylbis[(3S)-3-amino-4-(4-carboxy)phenylbutanoyl]bis(Bip-Phe benzamide)

This compound is obtained from compound 8 according to the protocol described in example 14. HPLC on a $C_8$ Kromasil 5 μM, 100 Å, 250×4.6 mm column, 1 ml/minute, $T_r$ (70% of B)=6.4 minutes. Mass $MH^+$=1428.8.

EXAMPLE 17

(2S)-2-2'-disulfanediylbis[(3S)-3-amino-4-(4-carboxy)phenylbutanoyl]bis(Bip-Bta benzamide)

This compound is obtained from compound 13 according to the protocol described in example 14. HPLC on a $C_8$ Kromasil 5 μM, 100 Å, 250×4.6 mm column, 1 ml/minute, $T_r$ (gradient from 40 to 100% of B over 20 minutes)=15.6 minutes. Mass $MH^+$=1541.0.

EXAMPLE 18

(2S)-2,2'-disulfanediylbis[(3S)-3-amino-4-(4-carboxy)phenylbutanoyl]bis(benzamide)

This compound is prepared by coupling the synthon described in example 1 with benzylamine in the presence of BOP and diisopropylamine in dichloromethane. The solvent is evaporated off and the product is washed under acid-base conditions. It is dried. The product is then deprotected as described above in example 1 and purified by semipreparative HPLC. It is oxidized to the disulfide as described above. HPLC on a $C_8$ Kromasil 5 μM, 100 Å, 250×4.6 mm column, 1 ml/minute, $T_r$ (35%)=5.6 minutes. Mass $MH^+$=689.8.

EXAMPLE 19

(2S)-2,2'-disulfanediylbis[(3S)-3-amino-4-(4-carboxy)phenylbutanoyl]bis(1-naphthylmethyl amide)

This compound is prepared by coupling the synthon described above in example 1 with 1-naphthalenemethylamine as described in example 2, i.e. in the presence of HOBT, diisopropylethylamine and EDCI in a minimum amount of DMF. The product is worked up as described in example 2. It is deprotected in the same manner (step 2 of example 2). It is purified by semipreparative HPLC. It is then oxidized to the disulfide as described above. HPLC on a $C_8$ Kromasil 5 μM, 100 Å, 250×4.6 mm column, 1 ml/minute, $T_r$ (gradient from 10 to 100% of B over 30 minutes)=15.0 minutes. Mass $MH^+$=787.9.

EXAMPLE 20

(2S)-2-2'-disulfanediylbis[(3S)-3-amino-4-(4-carboxy)phenylbutanoyl]bis(Bip-benzamide)

This compound is prepared according to the protocol described in example 2, using in the first step the benzylated amino acid amide Bip-NH-Bzl instead of the dipeptide ester Trp-Phe-OtBu, the only difference being that, after coupling, deprotection and purification, it is oxidized to the disulfide. HPLC on a $C_8$ Kromasil 5 μM, 100 Å, 250×4.6 mm column, 1 ml/minute, $T_r$ (gradient from 10 to 100% of B over 30 minutes)=20.5 minutes. Mass $MH^+$=1134.3.

EXAMPLE 21

2-2'-Disulfanediylbis[4-(4-carboxy)phenylpropanoyl]bis(benzamide)

Step 1. Synthesis of (2S)-2-(N-Boc)amino-3-[4-methyloxycarbonyl]phenylpropanoic acid The same method as for step 1 of example 1 is applied, but using methyl 4-bromomethylbenzoate.

Step 2. Synthesis of (2S)-2-amino-3-[4-methyloxycarbonyl]phenylpropanoic acid

The amine is deprotected using TFA in dichloromethane. The TFA and the DCM are then evaporated off. The product is then dried.

Step 3. Synthesis of (2R)-2-bromo-3-[4-methyloxycarbonyl]phenylpropanoic acid

The acid obtained above (1 equiv.) is mixed with aqueous 48% HBr solution at 0° C. in water, and 1.6 equiv. of $NaNO_2$ in water are then added. The mixture is stirred for 2 hours 30 minutes at room temperature. The nitrous vapors are evaporated off and the product is extracted with ether and dried.

Step 4. Synthesis of (2R)-2-thioacetate-3-[4-methyloxycarbonyl]phenylpropanoic acid The above product is dissolved in DMF (dimethylformamide) and 3 equiv. of potassium thioacetate are added. The reaction takes place overnight at room temperature. The mixture is then acidified and the product is extracted with ethy lacetate and dried.

Step 5. Synthesis of N-[(2S)-2-thioacetate-3-(4-methoxycarbonyl)phenylpropanoyl]benzamide The benzylamide is coupled with the above product as described above (first step of example 2).

Step 6.

The above product is treated with 0.5 N sodium hydroxide in methanol under an oxidizing atmosphere. After acidification, work-up and purification by semipreparative HPLC, the product is obtained in the form of a mixture of two stereoisomers. HPLC on a $C_{18}$ Kromasil 5 μM, 100 Å, 250×4.6 mm column, 1 ml/minute, $T_r$ (35% B)=8.1 and 8.63 minutes. Mass $MH^+$=629.7.

EXAMPLE 22

2,2'-Disulfanediylbis[4-(4-carboxy)phenylpropanoyl]bis(Bip-NH benzamide)

This product is obtained as for compound 21, but by coupling Bip-NHBzl in step 5. HPLC on a $C_{18}$ Kromasil 5 μM, 100 Å, 250×4.6 mm column, 1 ml/minute, $T_r$ (gradient from 10 to 100% of B over 30 minutes)=22.8 and 23.4 minutes. Mass $MH^+$=1076.3.

EXAMPLE 23

2,2'-Disulfanediylbis[4-(4-carboxy)phenylpropanoyl]bis(Bip Bta-benzamide)

This product is obtained as for example 21, but by coupling Bip Bta-NHBzl in step 5. HPLC on a $C_{18}$ Kromasil 5 μM, 100 Å, 250×4.6 mm column, 1 ml/minute, $T_r$ (gradient from 40 to 100% of B over 20 minutes)=17.4 and 18.1 minutes. Mass $MH^+$=1480.7.

EXAMPLE 24

Synthesis of 2,2'-disulfanediylbis[4-(4-carboxy)phenylpropanoyl]bis(Bip Bta-benzamide)

Step 1. Synthesis of tert-butyl 4-(3-bromo-3-carboxypropyl)benzoate

A solution of 0.291 g (3.7 eq) of potassium bromide in 0.87 ml of hydrobromic acid (0.75 M) is cooled to 0° C.

0.0874 g (1.9 eq) of sodium nitrite and a solution of 0.24 g (0.66 mM) of the tert-butyl ester compound of homophenylalanine (J. Org. Chem., 1987, 52, 5143–5150 and Bioorg. And Med. Chem. 2000, 8, 1677–1696) in 3 ml of hydrobromic acid (0.75 M) are successively added. The mixture is stirred at 0° C. for 90 minutes and 20 ml of cold ethyl acetate are added. This organic phase is recovered, washed with water and with saturated sodium chloride solution, and dried over sodium sulfate. After evaporation, a yellow oil is obtained, which is purified by chromatography (colorless oil, mass: 0.14 g (62%), Rf (c. Hex/EtOAc/AcOH: 7/3/0.5)= 0.19

Step 2. Synthesis of tert-butyl 4-(3-acetylsulfanyl-3-carboxypropyl)benzoate

A solution of 0.125 g (0.36 mM) of the ester obtained in step 1 in 0.364 ml of 1 N sodium hydroxide is cooled to 0° C. 0.05 g (1.2 eq) of potassium thioacetate is added and the mixture is stirred at room temperature for 48 hours. The resulting mixture is acidified to 0° C. with 1N hydrochloric acid solution. It is extracted with ethyl acetate and the organic phase is washed with water and with saturated sodium chloride solution. After drying and evaporation, a colorless oil is obtained. (Mass: 0.12 g, 98%). Rf (c.Hex/EtOAc/AcOH: 7/3/0.5)=0.11.

Step 3. Synthesis of 2,2'-bis[disulfanediylbis[4-tert -butoxycarbonylphenyl)butanoic acid]

A solution of 0.12 g (0.35 mM) of the ester from step 2 in 2 ml of methanol is cooled to 0° C. 0.7 ml (2.1 eq) of 1N sodium hydroxide solution is added and the mixture is stirred at room temperature for 30 minutes. A 0.25 M solution of iodine in ethanol is then added dropwise until a yellow color persists, and the mixture is acidified to pH 1–2 with 1N hydrochloric acid solution. The product is extracted with ethyl acetate, washed with water and dried (colorless oil, mass: 0.1 g (95%), Rf (c.Hex/EtOAc/AcOH: 6/4/0.5)= 0.25.

Step 4. Synthesis of 2,2'-disulfanediylbis[4-(4-carboxy)phenylpropanoyl]bis(Bip Bta benzamide)

This compound is prepared according to the protocol described in example 2, using, in the first step, the synthon from step 3 above instead of the synthon of example 1, and the dipeptide amide Bip-Bta-NHBzl instead of the dipeptide ester Trp-PheOtBu. HPLC on a Kromasil 5 μM, 100 Å, 250×4.6 mm column, 1 ml/minute, $T_r$: 25 minutes and 25.6 minutes, isocratic at 75% of B for 10 minutes and then gradient at 95% of B over 10 minutes, isocratic at 95% of B for 10 minutes.

The pseudodipeptide ester is then placed in contact with 0.13 μl/mg of anisole and 5 μl/mg of trifluoroacetic acid for 1 hour at room temperature. The reaction medium is evaporated and the product is precipitated from diethyl ether. The product is purified by semipreparative HPLC and freeze-dried. HPLC on Kromasil 5 μM, 100 Å, 250×4.6 mm column, 1 ml/minute, $T_r$: 15.3 minutes and 16.5 minutes, isocratic at 75% of B for 10 minutes and then gradient at 95% of B over 10 minutes, isocratic at 95% of B for 10 minutes. Mass (M−H)=1508.

EXAMPLE 25

Measurement of the Inhibitory Activity of the Illustrated Molecules Toward the Proteolytic Activity of BoNT/B Increasing amounts of inhibitors and 0.35 ng of the light chain of BoNT/B are preincubated in 100 μl final of HEPES 20 mM pH 7.4 buffer in the presence or absence of 0.1 mM DTT (dithiothreitol). 18 μM of the BoNT/B-specific substrate Syb 60–94 [$Pya^{74}$, $Nop^{77}$] are then added and the incubation is continued for 30 minutes at 37° C. The reaction is stopped by addition of 0.2 M HCl and the fluorescence reading is taken directly.

The amount of metabolite formed in each assay is determined from the fluorescence calibration curves. The Ki of the inhibitor is determined from the Cheng Prussof relationship: $Ki=IC_{50}/1+S/K_M$.

Inhibitory power toward type B botulinum toxin of the described examples

| Molecule | Example No. | Ki(BoNT/B) |
|---|---|---|
| 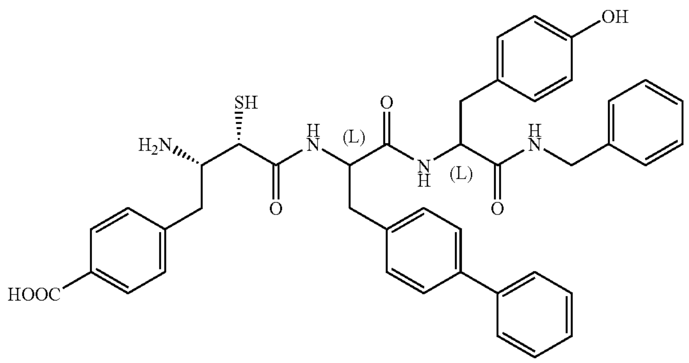 | Example 5 | $8.1 \times 10^{-7}$ M |

-continued
| Molecule | Example No. | Ki(BoNT/B) |
| --- | --- | --- |
| 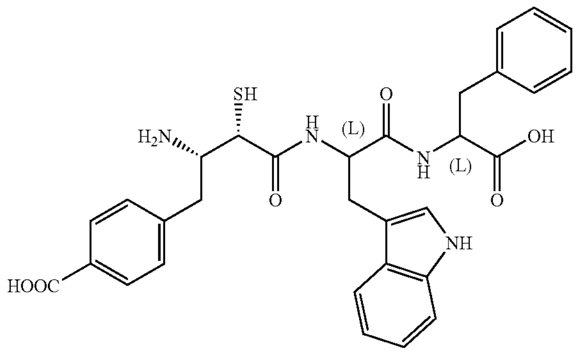 | Example 2 | $5.9 \times 10^{-7}$ M |
| 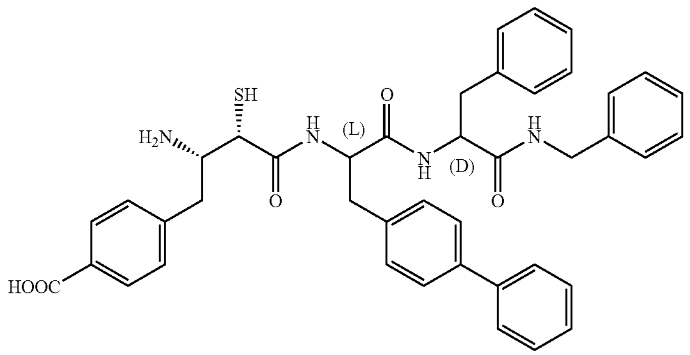 | Example 8 | $5.8 \times 10^{-7}$ M |
| 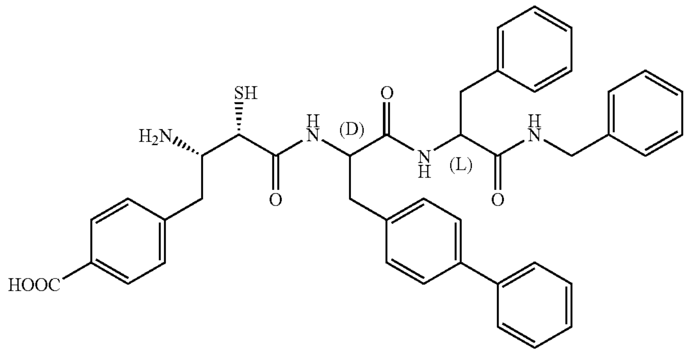 | Example 9 | $5.4 \times 10^{-7}$ M |
| 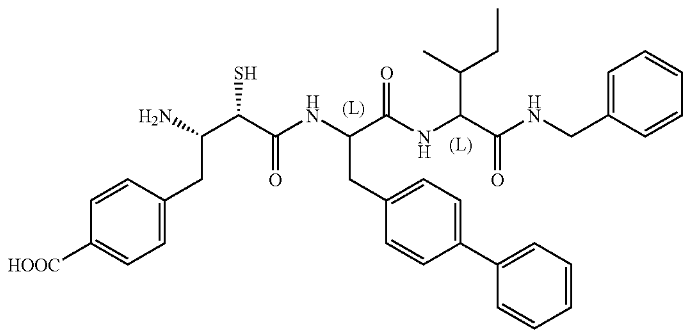 | Example 10 | $5.4 \times 10^{-7}$ M |

-continued
| Molecule | Example No. | Ki(BoNT/B) |
|---|---|---|
| 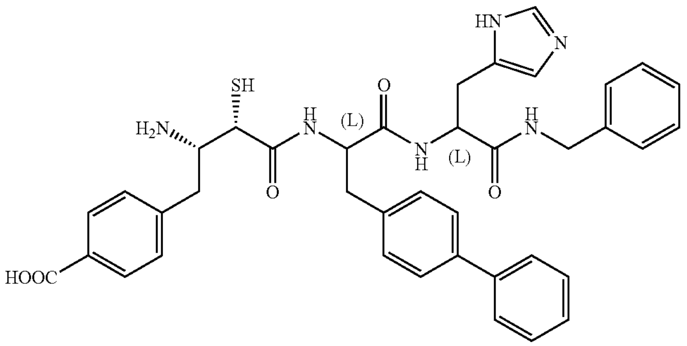 | Example 6 | $5.0 \times 10^{-7}$ M |
| 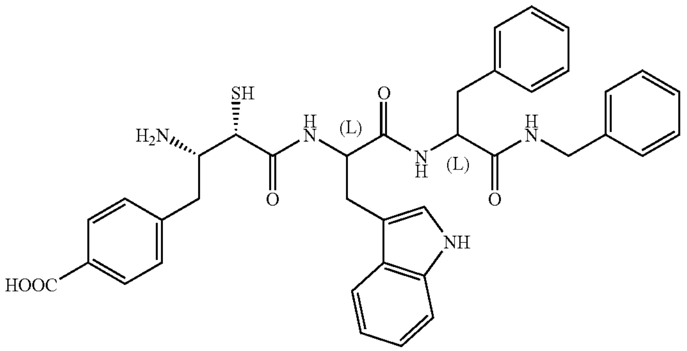 | Example 3 | $3.5 \times 10^{-7}$ M |
| 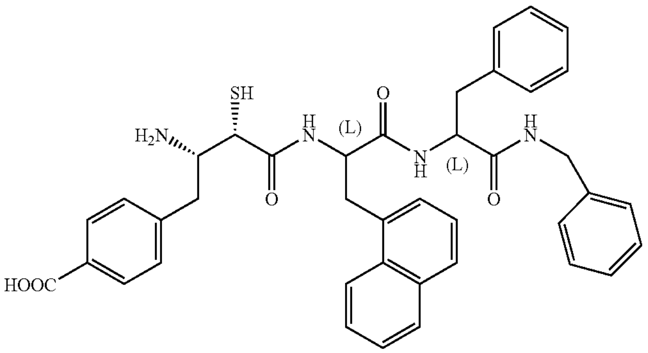 | Example 11 | $2.2 \times 10^{-7}$ M |
| 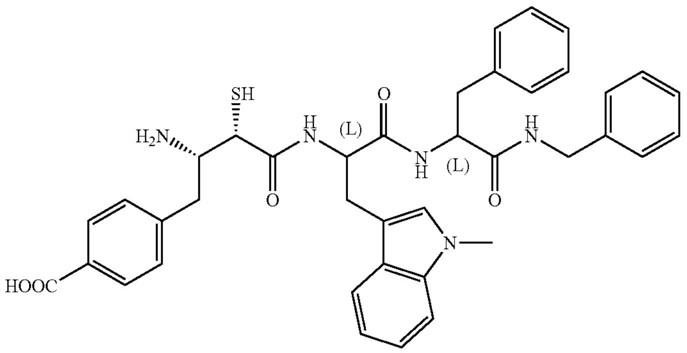 | Example 4 | $1.7 \times 10^{-7}$ M |

-continued
| Molecule | Example No. | Ki(BoNT/B) |
| --- | --- | --- |
| 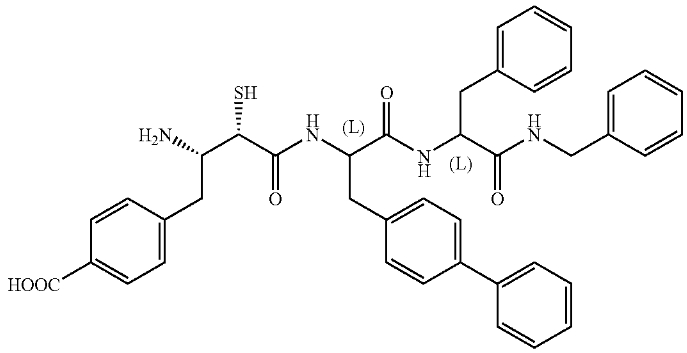 | Example 7 | $1.6 \times 10^{-7}$ M |
| 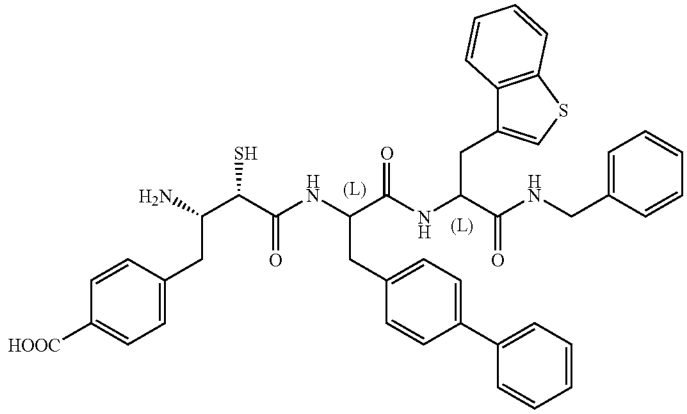 | Example 12 | $2.0 \times 10^{-8}$ M |
| 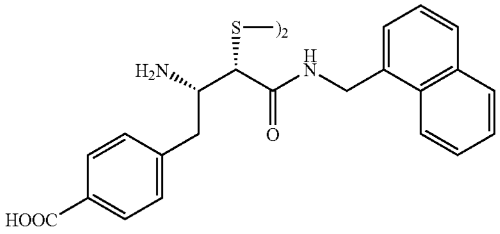 | Example 19 | $1.3 \times 10^{-6}$ M |
| 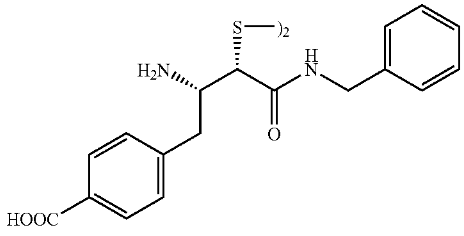 | Example 18 | $5.1 \times 10^{-7}$ M |
| 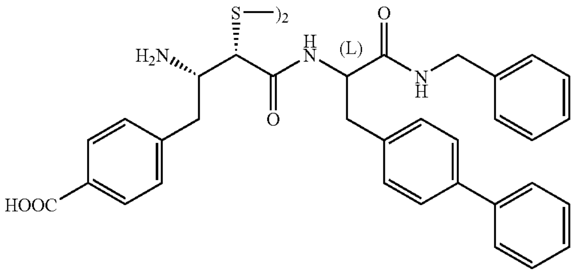 | Example 20 | $4.5 \times 10^{-8}$ M |

-continued
| Molecule | Example No. | Ki(BoNT/B) |
| --- | --- | --- |
| 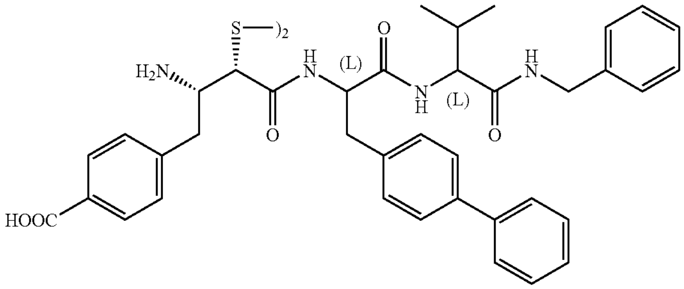 | Example 15 | $2.3 \times 10^{-8}$ M |
| 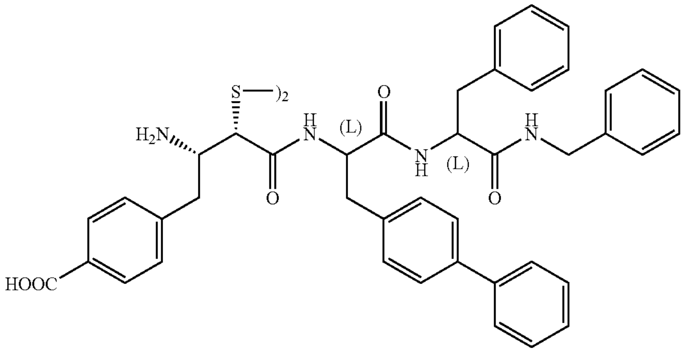 | Example 16 | $1.8 \times 10^{-8}$ M |
| 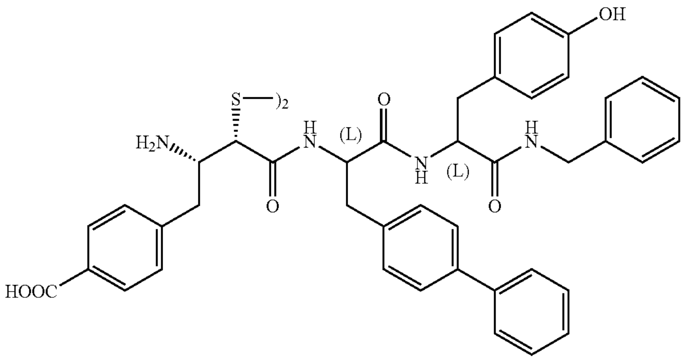 | Example 14 | $1.4 \times 10^{-8}$ M |
| 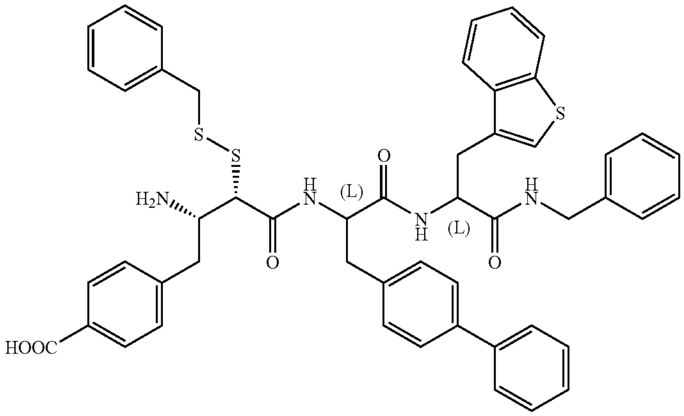 | Example 13 | $1.0 \times 10^{-8}$ M |

-continued
| Molecule | Example No. | Ki(BoNT/B) |
|---|---|---|
| 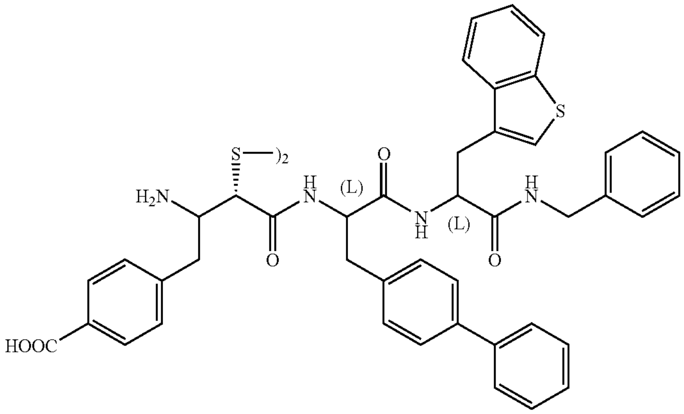 | Example 17 | $3.4 \times 10^{-9}$ M |
| 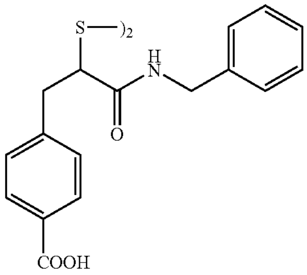 | Example 21 | $4.4 \times 10^{-7}$ M |
| 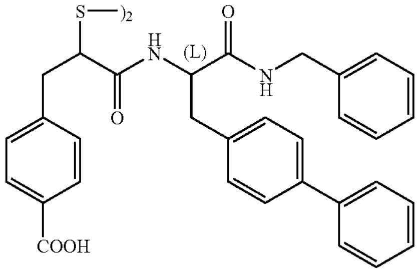 | Example 22 | $3.6 \times 10^{-8}$ M |
| 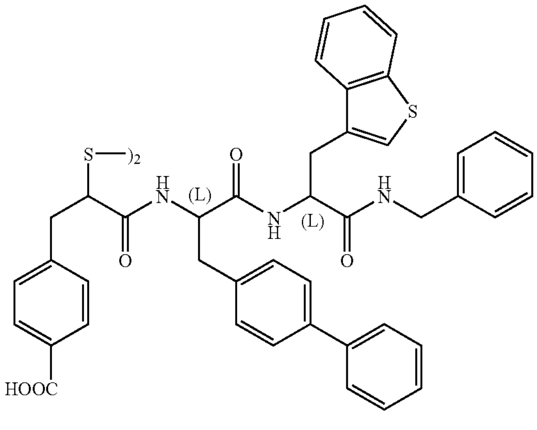 | Example 23 | $2.8 \times 10^{-9}$ M |

-continued

| Molecule | Example No. | Ki(BoNT/B) |
| --- | --- | --- |
| 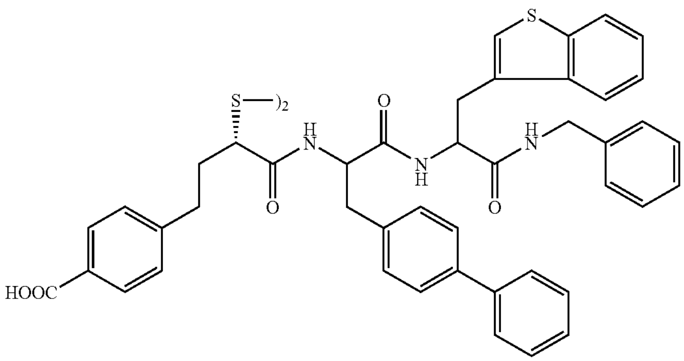 | Example 24 | $1.9 \times 10^{-9}$ M |

What is claimed is:

1. A compound of general formula (I):

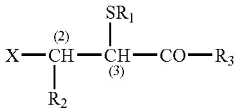

(I)

wherein:

(2) and (3) indicate two of the possible asymmetric centers in the molecule;

X is a hydrogen atom, a primary amine $NH_2$ or secondary amine NHR wherein R is an alkyl or arylalkyl group;

$R_1$ is:

a hydrogen atom, a group S-R' in which R' represents an alkyl, aryl, (aryl)alkyl, cycloalkyl or (cycloalkyl)alkyl group, or one of these groups substituted with at least one fluorine or other halogen atoms, or with a $CF_3$—; or a group S—CH[CH($R_2$)X]—CO—$R_3$ with $R_2$ and $R_3$ as defined below;

$R_2$ is an alkenyl, alkynyl, cycloalkyl, (cycloalkyl)alkyl, aryl or (aryl)alkyl group, substituted with a COOH or COOR" group, with R" being an alkyl, aryl, (aryl)alkyl, cycloalkyl or (cycloalkyl)alkyl group, substituted with at least one fluorine or other halogen atom, or with a $CF_3$ group;

$R_3$ is:

a group $NHR_4$ in which $R_4$ represents an alkyl, cycloalkyl, (cycloalkyl)alkyl, aryl, (aryl)alkyl, heteroaryl or (heteroaryl)alkyl group; or an amino acid residue or a peptide chain $(AA)_nR_5$ in which:

n is equal to 1 or 2

$R_5$ is OH, $NH_2$ or NHR'" with R'" being an alkyl, cycloalkyl, (cycloalkyl)alkyl, aryl, (aryl)alkyl, heteroaryl or (heteroaryl )alkyl group, AA is an amino acid residue of formula (II)

$$N(R_6)—(CH_2)_m—CH(R_7)—(CH_2)_p—CO \quad (II)$$

in which:

m=0 or 1, p=0 or 1, $R_6$ is a hydrogen atom, a methyl or another alkyl group; and $R_7$ is an alkyl, (aryl)alkyl or (heteroaryl)alkyl group, or one of these groups substituted with one or more halogen atoms and/or one or more group(s) selected from OH, $OCH_3$ or other alkoxy or $CF_3$, it being understood that, when n is equal to 2, the two amino acid residues AA may be identical or different;

and the addition salts or enantiomeric forms thereto.

2. The compound of claim 1, which is an addition salt of said compound of formula (I) with an acid, or a dimer of compounds of formula (I).

3. The compound of claim 1, wherein $R_1$ is a hydrogen atom or a group —S—CH[CH($R_2$)X]—CO—$R_3$, which may be identical to or different than the group of general formula I.

4. The compound of claim 1, wherein $R_2$ includes a group comprising at least one fused or non-fused aryl group.

5. The compound of claim 1, wherein $R_2$ is an aryl or arylalkyl group substituted with at least one carboxylic function.

6. The compound of claim 1, wherein $R_3$ is an amino acid residue or a peptide chain $(AA)_nR_5$.

7. The compound of claim 6, wherein n is equal to 2.

8. The compound of claim 6, wherein m and p are equal to zero.

9. The compound of claim 6, wherein AA is a group of general formula (II), in which the two groups $R_7$ are different and represent (aryl)alkyl or (heteroaryl)alkyl group.

10. The compound of claim 1, of general formula (Ia):

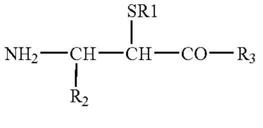

(Ia)

in which:

$R_1$— is a hydrogen atom or a group —S—CH[CH($R_2$)$NH_2$]$COR_3$, with $R_2$ and $R_3$ being as defined in claim 1;

$R_2$ is a (cycloalkyl)alkyl, aryl or (aryl)alkyl group, substituted with at least one COOH function;

$R_3$ is either a group $NHR_4$, with $R_4$ representing an alkyl, cycloalkyl, (cycloalkyl)alkyl, aryl, (aryl)alkyl, heteroaryl or (heteroaryl)alkyl group; or a group of formula (IIa):

$[NH(CH_2)_m—CHR_7(CH_2)_p]_nCOR_5$ (IIa)

in which:

n is equal to 1 and preferably 2, it being understood that, when n is equal to 2, the two groups given within the square brackets may be identical or different;

each of m and p, identical or different, is zero or 1, $R_7$ is an (aryl)alkyl or (heteroaryl)alkyl group, or one of these groups substituted with one or more halogen atoms and/or OH, $OCH_3$ or $CF_3$ group(s), and $R_5$ is an $NH_2$ or NHR''' group in which R''' is an alkyl, aryl, (aryl)alkyl, cycloalkyl or (cycloalkyl)alkyl group, or one of these groups substituted with at least one fluorine or other halogen atom, or with a $CF_3$ group.

11. The compound of claim 10, wherein $R_1$ is a group $—S—CH[CH(R_2)NH_3]COR_3$, with $R_2$ and $R_3$ as defined in claim 2.

12. The compound of claim 10, wherein m=p=0.

13. The compound of claim 1, which is of 2S, 3S configuration.

14. The compound of claim 1, which is selected from:

N-[(2S,3S)-2-sulfanyl-3-amino-4-(4-carboxyl-)phenyl) butanoyl]Trp-Phe;

N-[(2S,3S)-2-sulfanyl-3-amino-4-(4-carboxyl-)phenyl) butanoyl]-Trp-Phe benzamide;

N-[(2S,3S)-2-sulfanyl-3-amino-4-(4-carboxyl-)phenyl) butanoyl](N-Me)Trp-Phe benzamide;

N-[(2S,3S)-2-sulfanyl-3-amino-4-(4-carboxyl-)phenyl) butanoyl]Bip-Tyr benzamide;

N-[(2S,3S)-2-sulfanyl-3-amino-4-(4-carboxyl-)phenyl) butanoyl]Bip-His benzamide;

N-[(2S,3S)-2-sulfanyl-3-amino-4-(4-carboxyl-)phenyl) butanoyl]-Bip-Phe-benzamide;

N-[(2S,3S)-2-sulfanyl-3-amino-4-(4-carboxyl-)phenyl) butanoyl]Bip-D-Phe benzamide;

N-[(2S,3S)-2-sulfanyl-3-amino-4-(4-carboxyl-)phenyl) butanoyl]-D-Bip-Phe benzamide;

N-[(2S,3S)-2-sulfanyl-3-amino-4-(4-carboxyl-)phenyl) butanoyl]Bip-Ile benzamide;

N-[(2S,3S)-2-sulfanyl-3-amino-4-(4-carboxyl-)phenyl) butanoyl]1-Nap-Phe benzamide;

N-[(2S,3S)-2-sulfanyl-3-amino-4-(4-carboxyl-)phenyl) butanoyl]Bip-Bta benzamide;

N-[(2S,3S)-2-benzyldisulfanediyl-3-amino-4-(4-carboxy-)phenyl)butanoyl]-Bip-Bta benzamide;

(2S)-2,2'-disulfanediyl-bis[(3S)-3-amino-4-(4-carboxy-)phenyl)butanoyl]-bis(Bip-Tyr benzamide);

(2S)-2-2'-disulfanediylbis[(3S)-3-amino-4-(4-carboxy-)phenyl)butanoyl]bis(Bip-lle benzamide);

(2S)-2-2'-disulfanediylbis[(3S)-3-amino-4-(4-carboxy-)phenyl)butanoyl]bis(Bip-Phe benzamide);

(2S)-2-2'-disulfanediylbis[(3S)-3-amino-4-(4-carboxy-)phenyl)butanoyl]bis(Bip-Bta benzamide);

(2S)-2,2'disulfandiylbis[(3S)-3-amino-4-(4carboxy-)phenyl)butanoyl]bis(benzamide);

(2S)-2,2'-disulfanediylbis[(35)-3-amino-4-(4-carboxy-)phenyl)butanoyl]bis(1-naphthylmethylamide); and (2S)-2,2'-disulfanediylbis[(35)-3-amino-4-(4-carboxy-)phenyl)butanoyl]bis(Bip benzamide).

15. The compound of claim 1, of general formula (Ib):

(Ib)

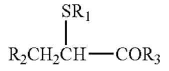

in which:

$R_1$ is a hydrogen atom or a group $—S—CH[CH(R_2)NH_2]COR_3$, with $R_2$ and $R_3$ being as defined in claim 1;

$R_2$ is a (cycloalkyl)alkyl, aryl or (aryl)alkyl group, substituted with at least one COOH function;

$R_3$ is either a group $NHR_4$, with $R_4$ being an alkyl, cycloalkyl, (cycloalkyl)alkyl, aryl, (aryl)alkyl, heteroaryl or (heteroaryl)alkyl group; or a group of formula (IIa):

$[NH(CH_2)_m—CHR_7—(CH_2)_p]_nCOR_5$ (IIa)

in which:

n is equal to 1 and preferably 2, it being understood that, when n is equal to 2, the two groups given within the square brackets may be identical or different;

each of m and p, identical or different, is zero or 1, $R_7$ is an (aryl)alkyl or (heteroaryl)alkyl group, or one of these groups substituted with one or more halogen atoms and/or OH, $OCH_3$ or $CF_3$ group(s), and $R_5$ is an $NH_2$ or NHR''' group in which R''' is an alkyl, aryl, (aryl)alkyl, cycloalkyl or (cycloalkyl)atkyl group, or one of these groups substituted with at least one fluorine or other halogen atom, or with a $CF_3$ group.

16. The compound of claim 15, wherein $R_1$ is a group $—S—CH[CH(R_2)NH_3]COR_3$.

17. The compound of claim 15, wherein m=p=0.

18. The compound of claim 15, which is selected from the following derivatives:

(2S)-2,2'-disulfanediylbis[4-(4-carboxy-)phenyl)propanoyl]bis(benzamide);

(2S)-2,2'-disulfanediylbis[4-(4-carboxy-)phenyl)propanoyl]bis(Bip benzamide); and (2S)-2,2'-disulfanediylbis[4-(4-carboxy-)phenyl)propanoyl]bis(Bip Bta-benzamide).

19. A process for preparing a compound of general formula (I) as claimed in claim 1, comprising a coupling reaction performed either of the synthon of general formula (IX):

(IX)

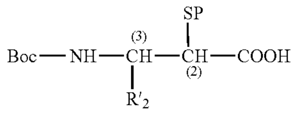

or of the synthon of general formula (XI):

(XI)

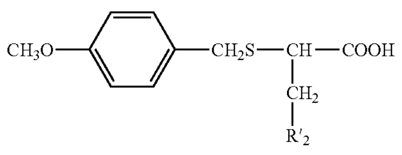

in which $R'_2$ is the protected form of $R_2$, with a group $R_3$ bearing an amide function, according to peptide synthesis, followed by the final deprotection of all the protecting groups.

20. The process as claimed in claim 19, wherein the symmetrical disulfide having the general formula (I) wherein $R_1$ represents $S—CH(CH(R_2)X)—CO—R_3$ is obtained by the action of an ethanolic solution of iodine on said compound of general formula (I) in which $R_1$ represents a hydrogen atom.

21. The process of claim 19, wherein the dissymmetric disulfide having the general formula (I) in which $R_1$ includes a group SR' as defined in claim 1 is obtained by the action on said compound of general formula (I), in which $R_1$ represents a hydrogen atom, of an activated disulfide of formula (X):

$$R'—S—S—COOCH_3 \quad (X)$$

in which R' represents an alkyl, aryl, (aryl)alkyl, cycloalkyl or (cycloalkyl)alkyl group, or one of these groups substituted with at least one fluorine of other halogen atom, or with a $CF_3$ group.

22. A pharmaceutical composition, comprising, as active principle, at least one compound of general formula (I) as defined in claim 1.

23. The pharmaceutical composition of claim 22, further comprising at least one pharmaceutically acceptable vehicle.

24. The pharmaceutical composition of claim 22, further comprising at least one clostridial toxin.

25. A diagnostic system for detecting botulinum neurotoxins, comprising at least one compound of general formula (I) as claimed in claim 1.

* * * * *

UNITED STATES PATENT AND TRADEMARK OFFICE

CERTIFICATE OF CORRECTION

PATENT NO. : 7,205,435 B2
APPLICATION NO. : 10/474378
DATED : April 17, 2007
INVENTOR(S) : Roques et al.

It is certified that error appears in the above-identified patent and that said Letters Patent is hereby corrected as shown below:

On the Title page: item (73) Assignee: change "Institut National de la Sante et de la Recherche Medicale (INSERM), Paris (FR); Centre National de la Recherche Scientifique (C.N.R.C.), Paris (FR)" to --Institut National de la Sante et de la Recherche Medicale (INSERM), Paris (FR); Centre National de la Recherche Scientifique (C.N.R.S.), Paris (FR) --

Signed and Sealed this

Twenty-sixth Day of June, 2007

JON W. DUDAS
*Director of the United States Patent and Trademark Office*